United States Patent [19]
Garrow

[11] Patent Number: 5,668,173
[45] Date of Patent: Sep. 16, 1997

[54] METHOD OF INCREASING THE CONVERSION OF HOMOCYSTEINE TO METHIONINE AND USES THEREOF

[75] Inventor: Timothy A. Garrow, Champaign, Ill.

[73] Assignee: The Board of Trustees of the University of Illinois Corp., Urbana, Ill.

[21] Appl. No.: 605,940

[22] Filed: Feb. 23, 1996

[51] Int. Cl.$^6$ .................................................. A61K 31/19
[52] U.S. Cl. .................................................. 514/557
[58] Field of Search .................................... 514/556, 557, 514/562

[56] References Cited

U.S. PATENT DOCUMENTS 5,139,791   8/1992   Nakajima et al. ........................ 426/2

*Primary Examiner*—Raymond Henley, III
*Attorney, Agent, or Firm*—Benjamin Aaron Adler

[57] ABSTRACT

The present invention provides a method of decreasing total plasma homocyst(e)ine levels in an animal in need of such treatment, comprising the step of administering to said animal a pharmacologically effective dose of a thetin. Further provided is a method of treating hyperhomocyst(e)inemia in an animal in need of such treatment, comprising the step of administering to said animal a pharmacologically effective dose of a thetin. Also provided are novel pharmaceutical and nutritional compositions. Further provided is a method of reducing or eliminating the costly supplementation of methionine, choline, and betaine to protein-containing animal feeds.

10 Claims, 8 Drawing Sheets

Adapted from Finkelstein, 1986.

OTHER SUBSTRATE (METHYL DONORS)/PRODUCT PAIRS

METHOD OF INCREASING THE CONVERSION OF HOMOCYSTEINE TO METHIONINE AND USES THEREOF

BACKGROUND OF THE INVENTION

1. Field of the Invention

The present invention relates generally to the fields of cardiovascular pharmacology and therapeutics, and animal nutrition. More specifically, the present invention relates to a method of decreasing plasma homocysteine levels in animals with hyperhomocyst(e)inemia. This invention also relates to a method of reducing or eliminating the supplemental methionine, choline, and betaine routinely added to animal feeds.

2. Description of the Related Art

Pharmaceutical or nutriceutical applications of the invention. Cardiovascular disease (CVD), i.e., coronary, cerebral, and peripheral atherosclerosis and thrombosis, is the major cause of death in the United States. The age-adjusted death rate from CVD decreased about 40 percent from 1964 to 1985 (1). This decline was attributed to better health care and lifestyle changes. Despite this decline, more than one fourth of all Americans still suffer from some form of CVD, and almost 50% die of this disease (2). The cost of CVD to Americans in direct health care expenditures and lost productivity is estimated to be $110 billion each year (2). This cost estimate is expected to rise since the population of elderly in this country is increasing.

The cause of CVD is multifactorial. Some well known risk factors include hypertension, smoking, and high blood cholesterol. Many risk factors are influenced by genetic predisposition and diet. It has been shown that hyperhomocyst(e)inemia is associated with the premature development of CVD (3, 4). Furthermore, there is evidence that suggest that the relationship between plasma homocysteine and CVD is causal and not just a marker for another risk factor since vascular lesions have been induced in primates by infusing homocysteine for a 3 month period. The risk of fatal thrombosis is reduced in homocystinurics undergoing plasma homocysteine-lowering treatment.

Fasting plasma homocysteine levels have been classified as either, normal (10–15 µM), or one of the following levels of hyperhomocyst(e)inemia; moderate (15–30 µM), intermediate (31–100 µM), or severe (>100 µM). Like blood cholesterol, the relationship of plasma homocysteine to CVD appears to be graded (5). This means that any increase in plasma homocysteine above normal is associated with an increased risk, and that the higher the elevation, the greater the risk. Several nutritional and genetic determinants have been identified that cause hyperhomocyst(e)inemia and some of these determinants are more common than previously imagined. The mechanistic details of how elevations in plasma homocysteine promote CVD is not completely understood.

Epidemiological reports indicate that 15–40% of CVD patients have elevated levels of plasma homocysteine (6). Studies have shown associations of plasma homocysteine with age, sex, smoking, hypertension, and total serum cholesterol (3, 4, 7). Plasma homocysteine increases with age and is higher in males than females. There is a positive linear association between plasma homocysteine and serum cholesterol levels. Both smoking and hypertension have multiplicative effects on plasma homocysteine (7).

The association of hyperhomocyst(e)inemia with some of the most potent risk factors for CVD, such as smoking, hypertension, and cholesterol metabolism, makes managing the levels of plasma homocysteine an important public health goal. An effective dietary or pharmaceutical treatment for hyperhomocyst(e)inemia would be expected to decrease the mortality and morbidity from CVD and result in considerable health care savings.

One of the most effective treatments for severe hyperhomocyst(e)inemia is the oral administration of pharmacological doses of betaine, either alone, or concurrent with vitamin supplementation. Betaine, a metabolite of choline oxidation, is a substrate for an enzyme called betaine-homocysteine methyltransferase. Betaine-homocysteine methyltransferase catalyzes the conversion of betaine and homocysteine to dimethylglycine and methionine, respectively. The treatment of hyperhomocyst(e)inemia with betaine reduces plasma homocysteine by increasing the conversion of homocysteine to methionine via the betaine-homocysteine methyltransferase catalyzed reaction. Normal levels of plasma homocysteine, however, are rarely attained by this treatment leaving considerable CVD risk for these individuals.

Animal feed applications relating to methionine. The animal feed industry typically formulates protein-containing organic feeds for domestic animal consumption. These feeds are often supplemented with various nutrients so that they meet the specific dietary requirements of a given animal species and therefore improve some measure of animal performance. Animal performance being defined herein as including but not limited to the physiological states of growth, gestation, and lactation.

Many feeds contain corn or soybean meal, or a mixture of these two feedstuffs, as a base ingredient. These feeds are routinely supplemented with methionine and choline to meet the recommended dietary intakes of these compounds (8–10). For example, methionine is typically added to these practical diets because they are often deficient in this essential amino acid. Choline also is added to these feeds. Although most animals do not have an absolute requirement for choline, and one notable exception is the chicken, choline is routinely added to animal feeds because it has methionine-sparing effects, that is, it reduces an animals dietary requirement for methionine. Betaine, a metabolite of choline oxidation, also is added to feeds for methionine- and choline-sparing effects. Some studies suggest that dietary betaine can reduce carcass fat in pigs and chickens and is effective in the treatment of diarrhea and wet litter in fowl.

In summary, the prior art is deficient in the lack of an effective methods to decrease plasma homocysteine levels in animals with hyperhomocyst(e)inemia. In addition, the prior art is deficient in a method to maximize the conversion of homocysteine to methionine while simultaneously decreasing the level of dietary methionine, choline and betaine added to animal feeds necessary to obtain optimal animal performance. The present invention fulfills this long-standing need and desire in the art.

SUMMARY OF THE INVENTION

Alternate methyl donor substrates for betaine-homocysteine methyltransferase, described herein, are more effective plasma homocysteine-lowering agents for the treatment of hyperhomocyst(e)inemia. This invention eliminates or reduces the supplemental methionine, choline, and betaine that is routinely added to practical animal feeds. This invention results in significant reductions in the cost of maintaining optimal animal performance.

In one embodiment of the present invention, there is provided a method of decreasing plasma homocysteine levels in an animal in need of such treatment, comprising the step of administering to said animal a pharmacologically effective dose of a thetin.

In another embodiment of the present invention, there is provided a pharmaceutical composition, comprising a thetin and a pharmaceutically acceptable carrier.

In another embodiment of the present invention, there is provided an animal feed supplement consisting essentially of a thetin selected from the group consisting of dimethylacetothetin and dimethylpropiothetin to lower the dietary requirement, and therefore feed supplement, of methionine, choline and betaine.

In yet another embodiment of the present invention, there is provided a method of treating hyperhomocysteinemia in an animal in need of such treatment, comprising the step of administering to said animal a pharmacologically effective dose of a thetin.

In yet another embodiment of the present invention, there is provided a nutritional supplement consisting essentially of a thetin selected from the group consisting of dimethylacetothetin and dimethylpropiothetin and at least one vitamin. The nutritional supplement may be taken either alone, or in combination with other dietary supplements.

In yet another embodiment of the present invention, there is provided a composition consisting essentially of a thetin selected from the group consisting of dimethylacetothetin and dimethylpropiothetin and choline. A further composition described herein consists essentially of a thetin selected from the group consisting of dimethylacetothetin and dimethylpropiothetin and betaine.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3A shows the reaction with betaine, a metabolite of choline oxidation. FIG. 3B shows alternate (thetin) methyl donor-product pairs for the betaine-homocysteine methyltransferase catalyzed reaction.

DETAILED DESCRIPTION OF THE INVENTION

The following abbreviations and definitions are used herein: The term "CVD" refers to cardiovascular disease. The term "plasma homocysteine" denotes total plasma homocyst(e)ine. The term "hyperhomocyst(e)inemia" denotes any level of total plasma homocyst(e)ine above normal.

Homocysteine metabolism

Homocysteine and methionine metabolism are related since methionine is the ultimate source of homocysteine in the body. An outline of homocysteine and methionine metabolism can be seen in FIG. 1. Methionine is an essential nutrient for many animals, and like all amino acids, is required for protein synthesis. Another role for methionine, however, depends upon its conversion to S-adenosylmethionine, an important compound used for many biological methylation reactions. When used in various methyltransferase reactions, S-adenosylmethionine is converted to S-adenosylhomocysteine, which in turn is hydrolyzed to produce homocysteine. Homocysteine lies at a metabolic branch point, it can be methylated to regenerate methionine by either methionine synthase (reaction 3, FIG. 1 ) or betaine-homocysteine methyltransferase (reaction 4, FIG. 1), or it can be metabolized to cysteine through the transsulfuration pathway. Transsulfuration is a catabolic pathway for methionine and begins with the physiologically irreversible condensation of serine and homocysteine by cystathionine-β-synthase (reaction 5, FIG. 1).

Figure 2:
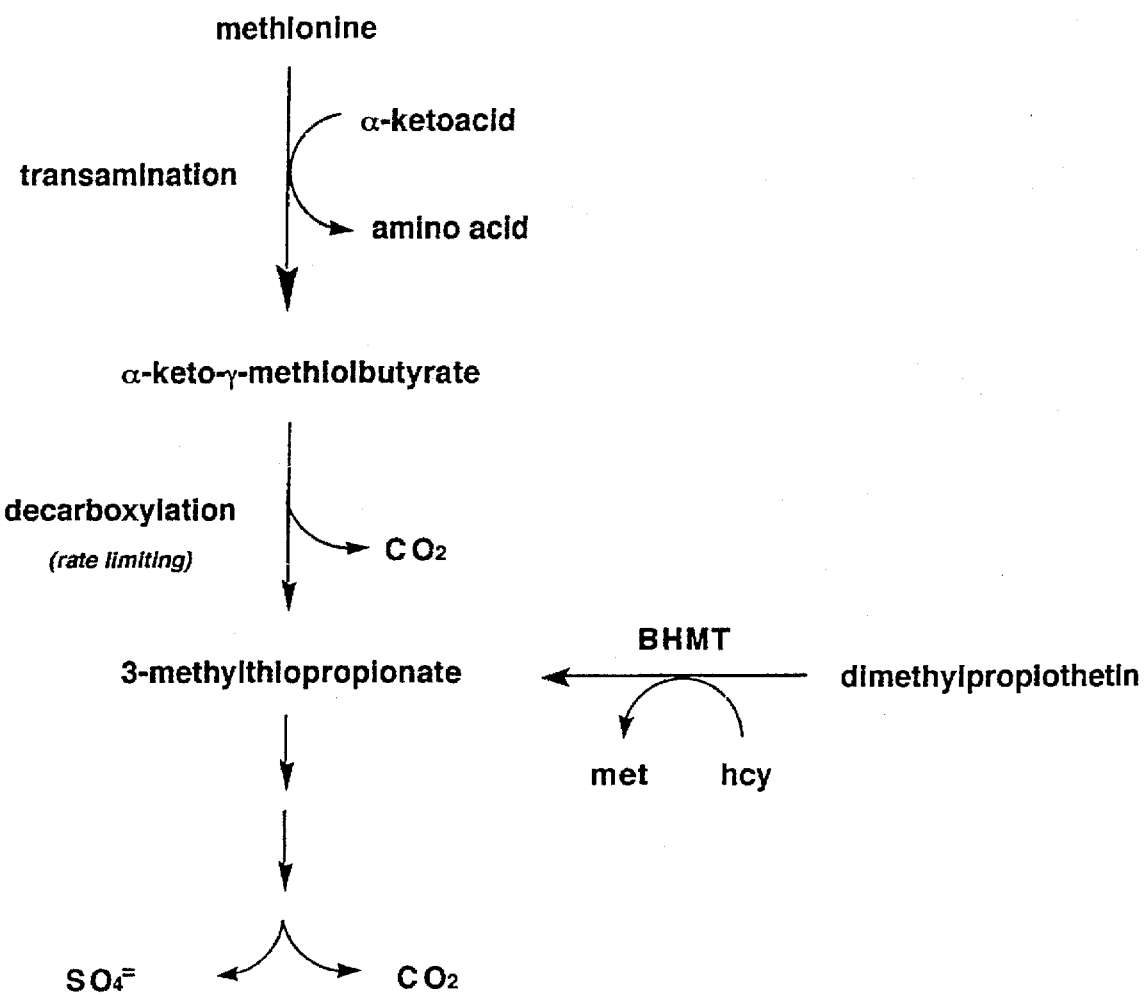
FIG. 2 shows the only known homocysteine-independent (transamination) pathway for methionine catabolism. Note that 3-methylthioproprionate is a proposed intermediate in this pathway. 3-Methylthiopropionate is a product of the betaine-homocysteine methyltransferase catalyzed reaction when dimethylpropriothetin is the methyl-donating substrate. Structures of 3-methylthioproprionate and dimethylpropriothetin can be seen in FIG. 3.

An alternate pathway (transamination) for methionine catabolism, that does not proceed through a homocysteine intermediate, has been described (11, 12), however, all of the enzymatic steps in this pathway have not been elucidated. This pathway is outlined in FIG. 2 and begins with a transamination step to form the α-keto acid of methionine, α-keto-γ-methiolbutyrate. This α-keto acid is then decarboxylated by α-keto-γ-methiolbutyrate decarboxylase to form 3-methylthiopropionate. This decarboxylase catalyzes the rate-limiting reaction in this pathway. Subsequent steps have not been fully characterized and the quantitative significance of this pathway to methionine catabolism, under normal or pathophysiological states, is unknown.

The factors that regulate homocysteine metabolism are poorly understood. It has been reported that humans consuming normal diets methylate approximately 50% of the available homocysteine while the remaining half proceeds through the transsulfuration pathway (13). However, the dietary intake of methionine influences the rate of transulfuration and methylation of homocysteine in rat liver. When dietary protein is in excess approximately 70% of the homocysteine is converted to cysteine and the labile methyl carbon on methionine turns over twice as fast (14). On low protein diets, only 10% of the available homocysteine proceeds through the transsulfuration pathway (14, 15). S-adenosylmethionine is an important modulator of these pathways since it is an allosteric activator (16) of cystathionine-b-synthase and a potent inhibitor (17) of methylenetetrahydrofolate reductase (refer to FIG. 1). Furthermore, a recent study shows that cystathionine-β-synthase activity and steady state levels of its mRNA decrease when dietary cysteine is increased (18).

With regard to the methylation of homocysteine, in vitro simulation studies indicate that methionine synthase and betaine-homocysteine methyltransferase contribute equally to this process (15). However, other studies have shown that methionine synthase and betaine-homocysteine methyltransferase activities change in response to various nutritional and hormonal treatments when measured in crude liver extract. Thus, the relative importance of one methyltransferase to the other may change depending upon physiological state (19, 20).

Hyperhomocyst(e)inemia: known causes and current treatments.

Figure 1:
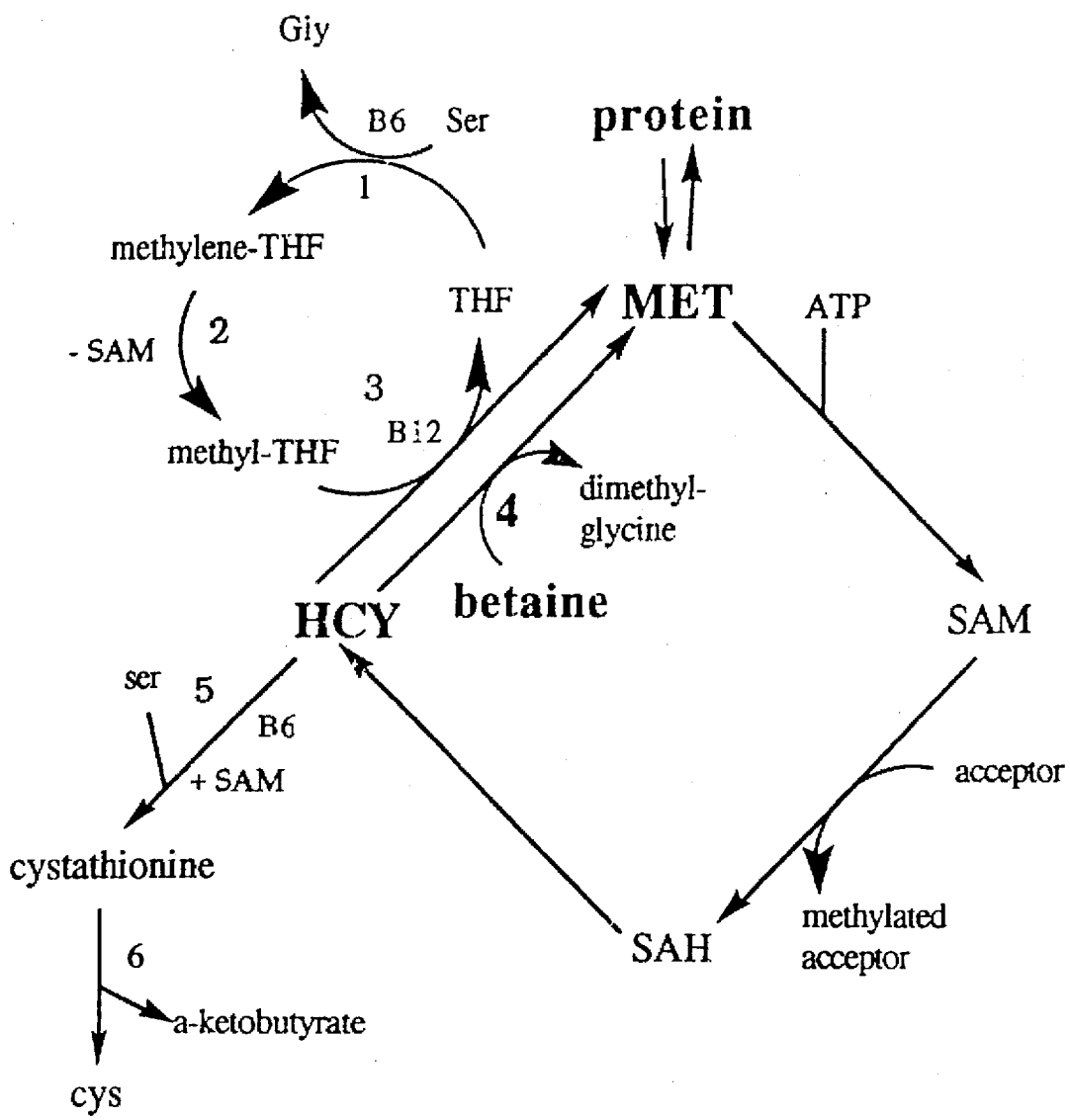
FIG. 1 shows an outline of homocysteine and methionine metabolism. Abbreviations: THF, tetrahydrofolate; SAM, S-adenosylmethionine; SAH, S-adenosylhomocysteine; HCY, homocysteine; ser, serine; cys, cysteine. Reactions: 1, serine hydroxymethyltransferase (vitamin $B_6$-dependent); 2, methylene-THF reductase; 3, methionine synthase ($B_{12}$-dependent); 4, betaine-homocysteine methyltransferase; 5, cystathionine-β-synthase (vitamin $B_6$-dependent); 6, cystathionase. Reactions 5 and 6 are referred to as the transsulfuration pathway. Deficiencies in reactions 2 and 5 cause hyperhomocyst(e)inemia in humans. Inborn errors of cobalamin metabolism also can cause hyperhomocyst(e)inemia in humans due to reduced availability of methyl cobalamin ($B_{12}$) for reaction 3.

Nutritional and genetic factors have been identified that cause some degree of hyperhomocyst(e)inemia in humans (FIG. 1). Nutrient deficiencies of either folate, vitamin B6, or vitamin B12, can result in moderate to intermediate hyperhomocyst(e)inemia in humans. Hyperhomocyst(e)inemia also can result from genetically determined deficiencies of key enzymes in homocysteine metabolism, namely, cystathionine-β-synthase or methylenetetrahydrofolate reductase activities, or inborn errors in the metabolism of vitamin B12 (cbl mutations). Cbl mutations cause hyperhomocyst(e)inemia by reducing the activity of vitamin B12-dependent methionine synthase. These genetic defects cause moderate to severe hyperhomocyst(e)inemia depending upon the nature of the mutation and whether both alleles are afflicted.

Nutritional therapies for hyperhomocyst(e)inemia have been implemented with some success. Individuals are usually supplemented with either folic acid, vitamin B12, vitamin B6, or a combination of these vitamins. Dietary methionine also has been restricted in cystathionine-β-synthase deficient patients. Individuals who are vitamin deficient, or who have genetic mutations that affect coenzyme affinity, respond favorably to this treatment. For example, approximately 50% of individuals with cystathionine-β-synthase deficiency respond to supplemental B6 whereas the remaining 50% are vitamin B6 nonresponsive. Some individuals with severe forms of cystathionine-β-synthase or methylenetetrahydrofolate reductase deficiency who have severe hyperhomocyst(e)inemia, do not respond to vitamin therapy. Pharmacological doses of betaine have been shown to reduce plasma homocysteine in these individuals (21-24). Betaine lowers plasma homocysteine by increasing the flux through betaine-homocysteine methyltransferase but this treatment does not usually lower plasma homocysteine to within the normal range, and the moderate to intermediate hyperhomocyst(e)inemia that persists confer considerable CVD risk for these individuals.

The betaine-homocysteine methyltransferase catalyzed reaction

Figure 3:
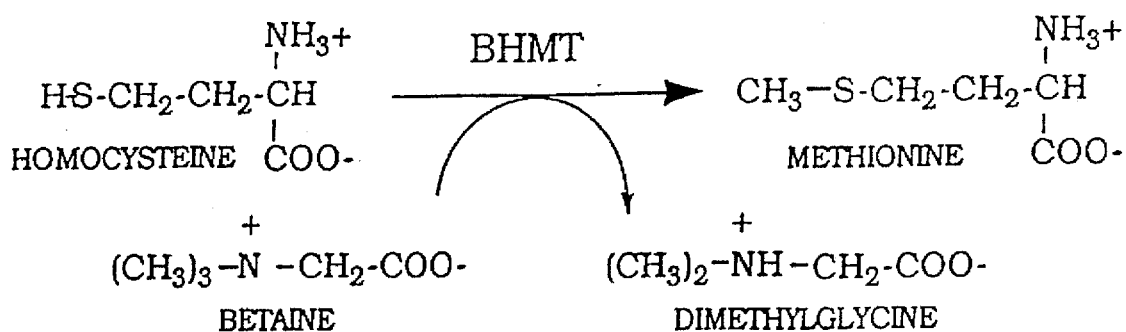
FIG. 3 shows the betaine-homocysteine methyltransferase catalyzed reaction. Betaine-homocysteine methyltransferase is an enzyme in the choline oxidation pathway.
Figure 3:
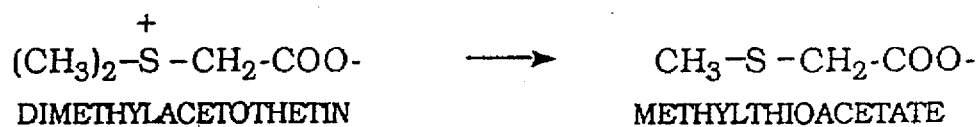
Figure 3:
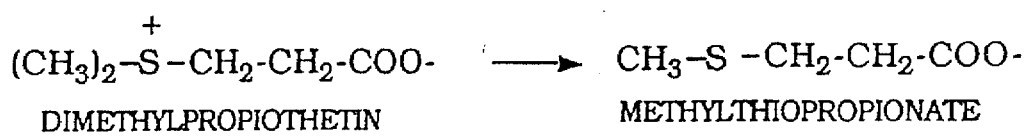
Figure 4:
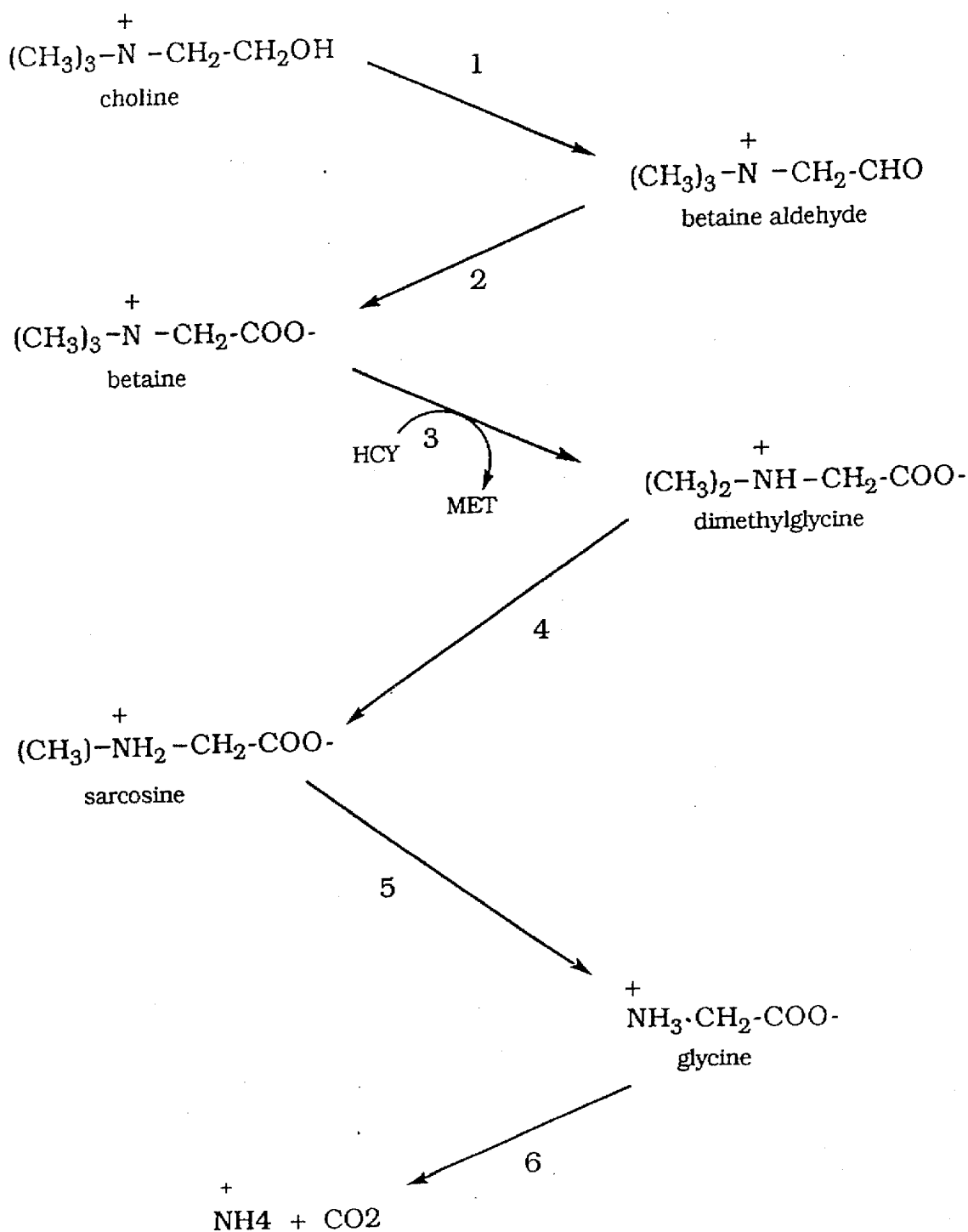
FIG. 4 shows the biochemical pathway of choline oxidation. Abbreviations: HCY, homocysteine; MET, methionine; THF, tetrahydrofolate; CH2THF, methylenetetrahydrofolate. Reactions: 1, choline dehydrogenase; 2, betaine aldehyde dehydrogenase; 3, betaine-homocysteine methyltransferase; 4, dimethylglycine dehydrogenase; 5, sarcosine dehydrogenase; 6, glycine cleavage. The oxidation of choline takes place primarily in the liver and kidney.

Betaine-homocysteine methyltransferase catalyzes the conversion of betaine and homocysteine to dimethylglycine and methionine, respectively (FIG. 3). This reaction is required for the oxidation of choline (FIG. 4). Betaine-homocysteine methyltransferase is primarily found in the liver and kidney of animals (25-27). Betaine-homocysteine methyltransferase has been purified from rat (28, 29), horse (30), human (31), and pig liver (32), an organ that expresses very high levels of this enzyme. Betaine-homocysteine methyltransferase is a hexamer of identical subunits of approximately 45 kDa.

Betaine-homocysteine methyltransferase activity is modulated by nutritional status. Finkelstein has reported higher levels of betaine-homocysteine methyltransferase activity in crude liver extracts when rats consume surfeit levels of dietary choline, betaine, or methionine compared to control animals (33, 34). In addition, methionine deficiency also elevates hepatic betaine-homocysteine methyltransferase activity. Similar effects of dietary methionine, choline, and betaine intakes on hepatic betaine-homocysteine methyltransferase activity have been observed in chickens. These findings suggest that betaine-homocysteine methyltransferase functions to conserve homocysteine when dietary methionine is low, and metabolize excess betaine. Excess betaine can be provided either preformed in the diet or produced from excess dietary choline. Betaine-homocysteine methyltransferase activity also has been reported to be influenced by hormonal status.

Kinetic studies of the betaine-homocysteine methyltransferase catalyzed reaction have been limited. There are several reports describing alternative substrates as methyl donors, and the ability of products, or substrate and product analogs, to inhibit the betaine-homocysteine methyltransferase reaction (25, 29, 31, 35, 36, 37). The Michealis constants for betaine and homocysteine have been estimated using rat and human betaine-homocysteine methyltransferase containing extracts and are reportedly in the 25-50 μM range.

The kinetic mechanism of betaine-homocysteine methyltransferase has been evaluated using partially purified rat enzyme (28, 38). Both studies concluded that the reaction mechanism was sequential. One study suggested that the reaction is ordered with homocysteine being the first substrate to bind, and methionine being the last product to come off the enzyme, however, data were not presented to substantiate their conclusions.

Thetins are alternate substrates for the betaine-homocysteine methyltransferase reaction and increase the conversion of homocysteine to methionine Several studies have shown that dimethylacetothetin and dimethylpropiothetin are substrates for betaine-homocysteine methyltransferase (FIG. 3). These studies assayed betaine-homocysteine methyltransferase activity using saturating levels of substrates, and in each case, after correcting for different enzyme concentrations, more methionine was produced with thetins as methyl donors than when betaine was used. Prior studies have shown that these thetins can replace dietary choline and betaine and are non-toxic to animals. Furthermore, dimethylpropiothetin is a compound that is synthesized by some salt-tolerant plants and marine animals.

Initial rate studies of the homocysteine-dependent betaine-homocysteine methyltransferase catalyzed demethylation of dimethylacetothetin can be found in Example I below. These studies clearly show that dimethylacetothetin displays greater specificity (Vmax/Km) for the betaine-homocysteine methyltransferase reaction than betaine. The product of the dimethylacetothetin-dependent reaction has lower affinity to betaine-homocysteine methyltransferase than does the product of the betaine-dependent reaction. The literature cited above, and the studies reported below, indicate that thetins will increase the rate of methionine formation from homocysteine and will be effective as plasma homocysteine-lowering agents and as feed additives with methionine-, choline-, and betaine-sparing effects.

The present invention is directed to a method of decreasing plasma homocysteine levels in an animal in need of such treatment, comprising the step of administering to said animal a pharmacologically effective dose of a thetin compound or biochemically similar analogue thereof. Preferably, the methods of the present invention will be useful in humans. Even more preferably, a method of decreasing homocysteine levels in an animal who has hyperhomocyst(e)inemia will be useful.

Generally, any thetin which decreases or inhibits the physiological levels of homocysteine in the animal will be useful in the methods of the present invention Preferably, the thetin is selected from the group consisting of dimethylacetothetin and dimethylpropriothetin, and any salts or analogues thereof. Specifically contemplated analogues include ester analogues of dimethylacetothetin and dimethylpropriothetin, i.e, methyl ester, ethyl ester, etc.

Generally, the thetin compounds may be administered in the methods of the present invention in any concentration which decreases physiological levels of homocysteine in the animal. Preferably, the thetin is administered in a dose of from about 1 mg mg/kg to about 50 mg/kg. Betaine and thetins are of approximately the same molecular weight. The pharmacological doses of betaine given to patients with severe hyperhomocyst(e)inemia is 3–6 grams/day. If average person is 50–70 kg, e.g., 60 kg, then they are getting approximately 50–100 mg/kg body weight per day. Treatment for more mild forms of hyperhomocyst(e)inemia or other related pathologies elevating plasma homocysteine would likely require less. Furthermore, a human on average consumes 500 g of food per day (dry weight basis). Then 5 g would be about 1% of the diet. For animal feed supplements, up to about 0.75% of the diet on a dry weight basis would be useful.

The present invention is also directed to a pharmaceutical composition, comprising a thetin and a pharmaceutically acceptable carrier. In the pharmaceutical composition, the thetin is preferably selected from the group consisting of dimethylacetothetin and dimethylpropriothetin, and any salts or analogues thereof.

The present invention is also directed to an animal feed supplement consisting essentially of a thetin selected from the group consisting of dimethylacetothetin and dimethylpropriothetin or any salts or analogues thereof as a means of decreasing the feed levels of methionine, choline, and/or betaine while maintaining optimal animal performance. This invention is applicable to the diet of animals, which herein is defined as including fowl and mammals.

The present invention is also directed to a method of treating hyperhomocyst(e)inemia in an animal in need of such treatment, comprising the step of administering to said animal a pharmacologically effective dose of a thetin.

It is specifically contemplated that the present invention may be used in combination with more conventional therapies. For example, thetin(s) may be used in combination with betaine, choline, and/or vitamins and other nutritional therapies. Thus, the present invention also is directed to a nutritional supplement consisting essentially of a thetin selected from the group consisting of dimethylacetothetin and dimethylpropriothetin and at least one vitamin. The nutritional supplement may be taken either alone, or in combination with other dietary supplements.

In yet another embodiment of the present invention, there is provided a composition consisting essentially of a thetin selected from the group consisting of dimethylacetothetin and dimethylpropiothetin and choline. A further composition described herein consists essentially of a thetin selected from the group consisting of dimethylacetothetin and dimethylpropiothetin and betaine. Concentrations of choline and betaine useful in these compositions are well known to those having ordinary skill in the art.

The following examples are given for the purpose of illustrating various embodiments of the invention and are not meant to limit the present invention in any fashion.

EXAMPLE 1

Purification of pig liver betaine-homocysteine methyltransferase and enzyme kinetics: comparison of betaine and dimethylacetothetin as methyl donors Betaine was prepared and purified by procedures that have been previously described (39, 40). The chloride salts of dimethylacetothetin and dimethylpropiothetin were synthesized by two general methods (41, 42). In brief, one approach used equimolar amounts of methylsulfide, and either iodo- or chloro-acetic acid for dimethylacetothetin synthesis, or iodopropionic acid for dimethylpropiothetin synthesis. Ethyl alcohol or ether were used as reaction solvents. A second approach used equal molar concentrations of methyl iodide and either methylthioacetic, or methylthioproprionic acid, in aqueous formic acid. When necessary, treatment with silver chloride, and subsequent removal of silver iodide by filtration, was performed to make the chloride salts. Following filtration or evaporation steps, thetins were purified by recrystallization from hot ethanol with ether. Structures and purities were verified by proton nuclear magnetic resonance. Radiolabeled ($^{14}$C) dimethylacetothetin chloride was prepared by reacting methylsulfide with $^{14}$C-labeled iodoacetic acid.

Betaine-homocysteine methyltransferase assay

Betaine-homocysteine methyltransferase activity was measured as described by Finkelstein and Mudd (43) with the following minor modifications. Routine measurements used 5 mM D,L-homocysteine and 2 mM betaine (0.05–0.1 µCi), respectively, in a final reaction volume of 0.5 mL. Following a 2 hour incubation, samples were chilled to 0° C. and 2.5 mL ice-cold water was added. The samples were loaded onto a 0.5 cm (diameter) column containing 1 mL of Dowex 1-X4 (OH—) resin (100–200 mesh). The unreacted betaine (or dimethylacetothetin) was washed from the column with water (3×5 mL), and dimethylglycine (or methylthioacetate) and methionine eluted into scintiallation vials with 3 mL 1.5 N HCl. Blanks contained all of the reaction components except enzyme and their values were subtracted from the sample values. All samples were assayed in duplicate.

Michealis and Vmax constants were estimated from plotting initial rate data according to the method of Hanes (44). Kinetic assays used L-homocysteine instead of D,L-homocysteine. Substrate concentrations were varied where appropriate at fixed levels of either betaine (250 µM) or L-homocysteine (500 µM).

Enzyme Purification

Betaine-homocysteine methyltransferase has been purified to homogeneity from pig liver (45). A typical purification and sodium dodecylsulfate polyacrylamide electrophoretic analysis of a purified fraction can be seen in TABLE I and FIG. 8, respectively.

TABLE I

Purification of pig liver betaine-homocysteine methyltransferase

| fraction | activity* (units/mg) | x-fold purification | yield (%) |
| --- | --- | --- | --- |
| crude | 14.4 | 1 | 100 |
| heat treated | 38.7 | 3 | 96 |
| hydroxylapatite | 552 | 38 | 58 |
| phenyl sepharose | 938 | 65 | 8 |
| DEAE cellulose | 1367 | 95 | 6 |

*units are nmole methionine formed per hour. kcat ~0.02/sec.

Using purified enzyme, initial rate studies were performed to determine the Michaelis constants of betaine, dimethylacetothetin, and homocysteine and to investigate the kinetic mechanism of the enzyme. Using saturating levels of one substrate while varying the other, Michaelis constants were estimated to be 23, 32, and 155 µM for betaine, L-homocysteine, and dimethylacetothetin, respectively. As can be seen in TABLE II, the relative Vmax obtained using dimethylacetothetin was 47-fold greater than when betaine was used for the methylation reaction. The Vmax/Km using dimethylacetothetin was 7-fold greater than that for betaine indicating that this methyl donor has greater specificity for betaine-homocysteine methyltransferase. Thus, when present at equimolar concentrations as betaine, the dimethylacetothetin-dependent methylation of homocysteine would proceed at least 700% faster.

TABLE II

| Substrate | Km(µM) | Vmax(rel)† | Vmax/Km(rel) |
| --- | --- | --- | --- |
| betaine | 23 | 1 | 1 |
| dimethyl-acetothentin | 155 | 7 | 47 |

†Relative indicates maximum velocity corrected for an equivalent amount of enzyme.

Dimethylacetothetin and dimethylpropiothetin have previously been shown to be substrates for betaine-homocysteine methyltransferase (25, 28, 30, 36). These prior studies assayed betaine-homocysteine methyltransferase using saturating levels of either betaine or thetin, (millimolar concentrations whereas the $K_m$ for betaine is ~20–50 µM). Depending on the source of betaine-homocysteine methyltransferase, significant increases in methionine production were observed. For example, when dimethylpropiothetin or dimethylacetothetin were assayed as methyl donors using purified horse betaine-homocysteine methyltrasferase, 54- and 350-fold increases in methionine production were observed when compared to betaine (30). These estimates would be analogous to Vmax comparisons since no substrate inhibition has been detected. The significantly higher Vmax observed for the dimethylacetothetin-dependent reaction relative to the betaine-dependent reaction reported here (TABLE II) are consistent with previous reports.

Initial velocity data using subsaturating levels of both betaine and homocysteine produced a family of double reciprocal plots that were linear when homocysteine was varied at different fixed concentrations of betaine. These lines converge at a positive 1/velocity and negative 1/substrate value indicating that the enzyme reaction is sequential (46). This mechanism precludes the formation of product until a ternary complex of substrates and enzyme is formed. Sequential kinetics also have been reported for rat betaine-homocysteine methyltransferase.

Figure 5:
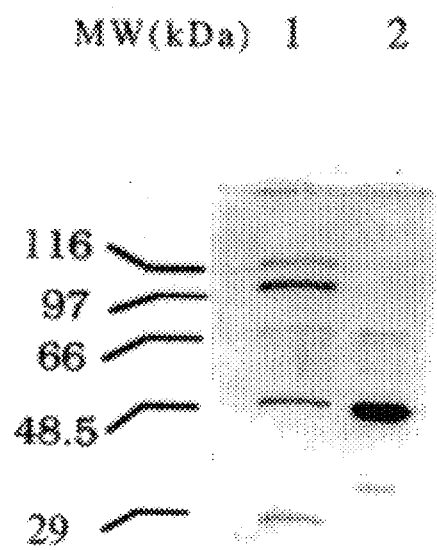
FIG. 5 shows sodium dodecylsulfate polyacrylamide electrophoretic analysis of pig liver betaine-homocysteine methyltransferase. Lane 1, MW standards. Lane 2, DEAE cellulose purified enzyme.
Figure 6:
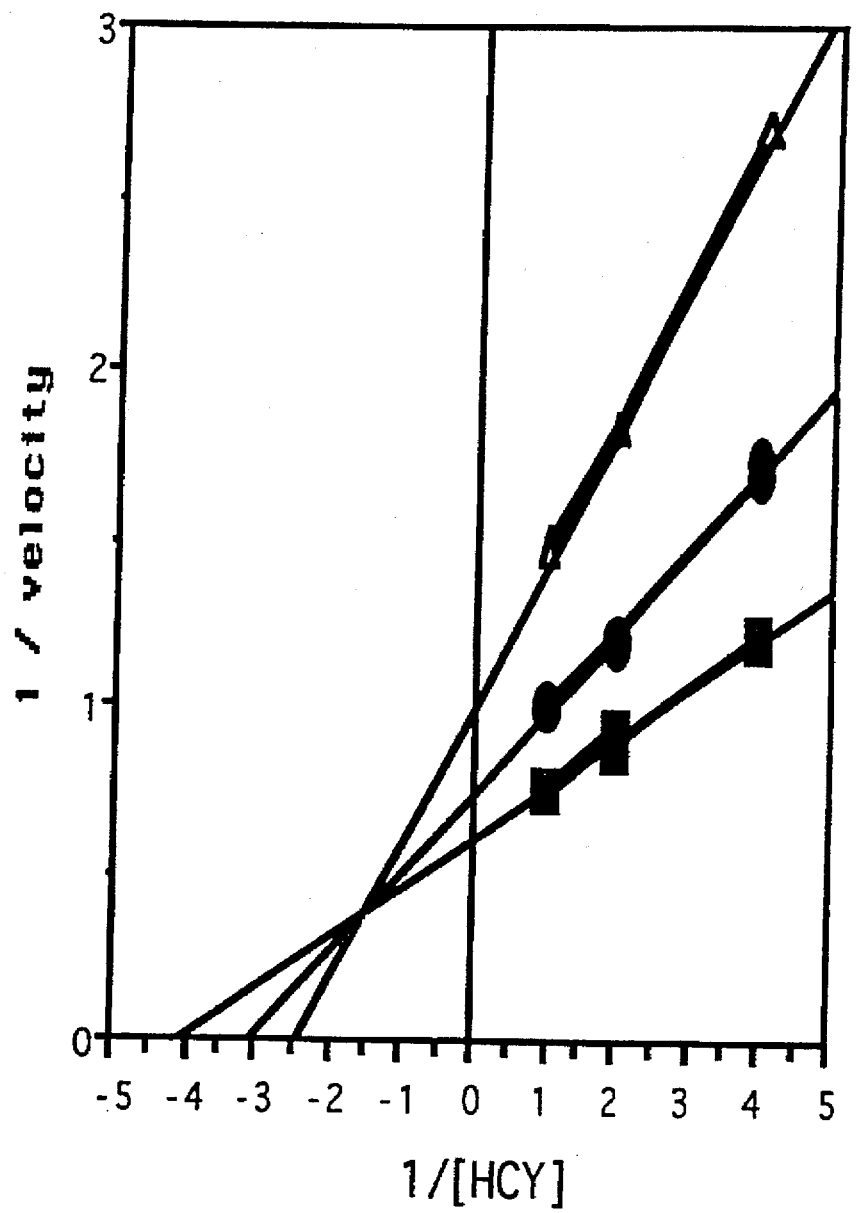
FIG. 6 shows a Lineweaver-Burke plot of initial rate velocities of pig liver betaine-homocysteine methyltransferase activity using subsaturating concentrations of betaine (fixed: 25, 50, 100 μM) and homocysteine (variable). The converging family of lines indicate that the kinetic mechanism is sequential.
Figure 7A:
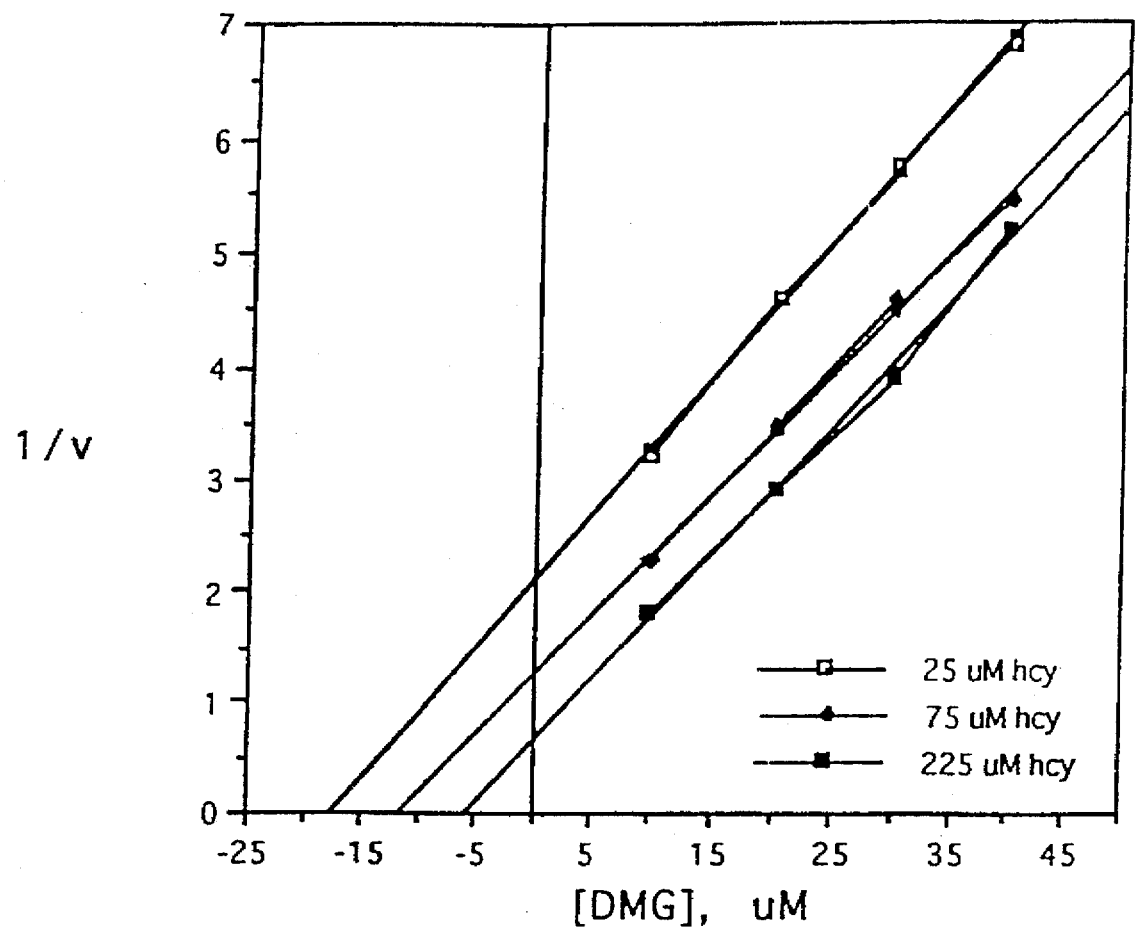
FIG. 7 shows the inhibition (Dixon plots) of purified pig liver betaine-homocysteine methyltransferase activity by dimethylglycine. Betaine was fixed at 25 μM (panel A) or 250 μM (panel B) while L-homocysteine was varied. Parallel lines indicate uncompetitive inhibition relative to homocysteine.
Figure 7B:
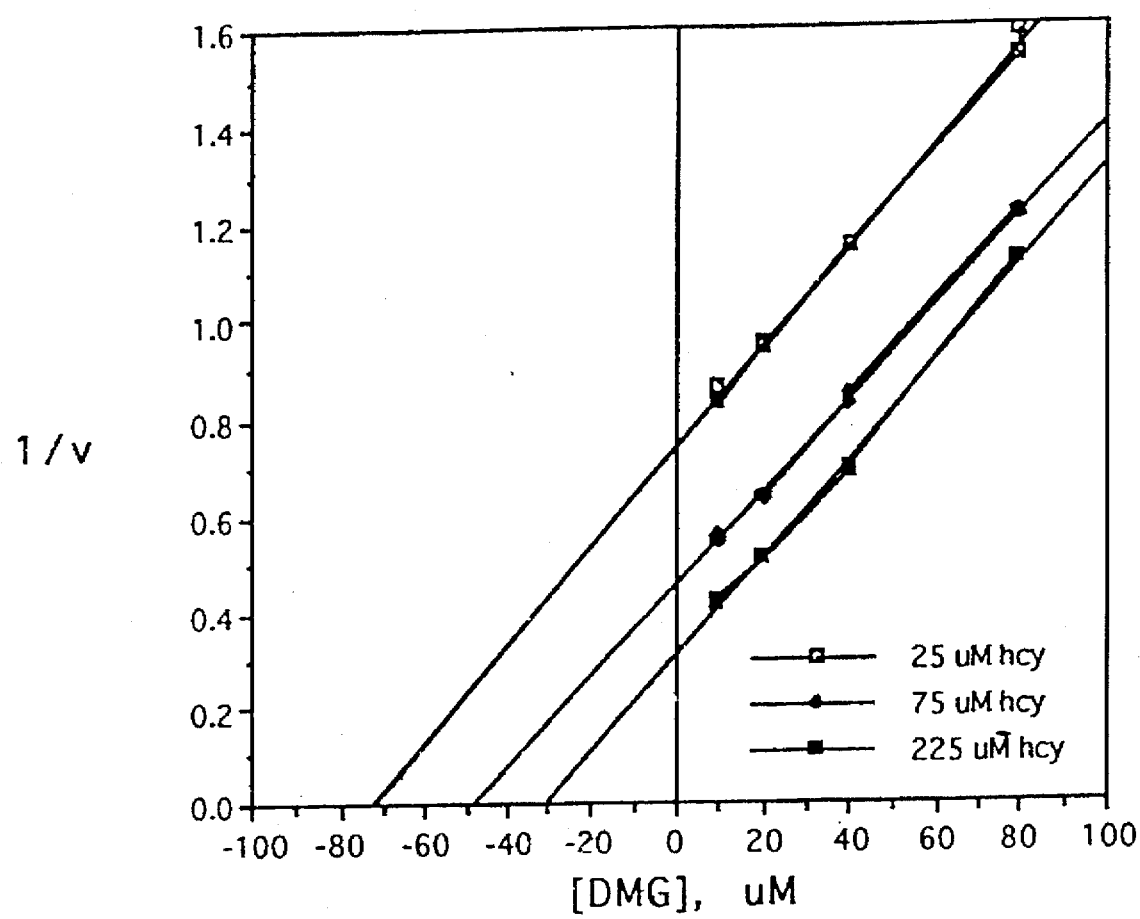

Product inhibition studies indicate that dimethylglycine is a potent inhibitor of pig betaine-homocysteine methyltransferase (FIG. 5). Methylthioacetate, the product of the dimethylacetothetin-dependent reaction, has lower affinity for betaine-homocysteine methyltransferase than dimethylglycine (TABLE III). The significantly higher Vmax of the dimethylacetothetin-dependent reaction relative to betaine is likely due, in part, to the reduced affinity of methylthioacetate for betaine-homocysteine methyltransferase relative to dimethylglycine. The subsequent metabolism of these products could have significant effects on flux through the betaine-homocysteine methyltransferase reaction because the rate of product removal would determine whether a product accumulates enough to inhibit enzyme activity. When pharmacological doses of betaine is used for the treatment of severe hyperhomocyst(e)inemia, dimethylglycine oxidation appears to be insufficient, and as a result, dimethylglycine accumulates.

TABLE III

Inhibition pf pig liver betaine-homocysteine methyltransferase activity by dimethyglycine ethylthoacetate in the presence of subsaturating levels of L-homocysteine (50 µM) and betaine (25 µM).

| inhibitor (50 µM) | pmol methionine | % activity |
| --- | --- | --- |
| none | 700 | 100 |
| dimethylglycine | 208 | 30 |
| methylthioacetate | 416 | 59 |

Although the initial rate kinetics for the dimethylpropiothetin-dependent reaction have not been evaluated, this reaction will likely have a lower Vmax/Km than the dimethylacetothetin-dependent reaction. Although previous studies indicate that the dimethylpropiothetin-dependent methyl transfer has a higher Vmax than the betaine-dependent reaction, in every case it has been shown to have a lower Vmax than the dimethylacetothetin-dependent reaction.

It is an object of the present invention to define the kinetic scheme for pig liver betaine-homocysteine methyltransferase and determine the kinetic constants of dimethylpropiothetin for the betaine-homocysteine methyltransferase catalyzed reaction.

EXAMPLE 2

Betaine is only partially effective for the treatment of hyperhomocyst(e)inemia

Although treating severe hyperhomocyst(e)inemia with betaine generally lowers plasma homocysteine compared to pretreatment levels, plasma homocysteine usually does not fall within the normal range. Since the relationship between CVD and plasma homocysteine is graded, the inability of betaine treatment to completely normalize plasma homocysteine leaves significant CVD risk for these individuals (35, 47). The inability of betaine treatment to normalize plasma homocysteine is likely related to the kinetic properties of the betaine-homocysteine methyltransferase reaction.

It has been shown that concomitant with a decrease in plasma homocysteine during betaine treatment, there is also a dramatic increase in plasma (35) and urinary (48) betaine and dimethylglycine. Increases in plasma concentrations of betaine and dimethylglycine have been reported to be 50 to 200-fold and 40 to 125-fold, respectively. These metabolites are usually not detected in urine. The accumulation of betaine and dimethylglycine is likely related to the fact that the betaine-dependent reaction has a very low Kcat that is, at least in part, due to the high affinity dimethylglycine has for the enzyme (29, 31 and table 1).

Dimethylglycine has been reported to be a potent inhibitor of human (31, 35), and rat (38) betaine-homocysteine methyltransferases. Herein, dimethylglycine was an uncompetitive inhibitor of pig betaine-homocysteine methyltransferase activity when homocysteine concentrations were varied at either subsaturating (25 µM), or saturating (250 µM) concentrations of betaine (FIG. 5). It is possible that homocysteine, dimethylglycine, and betaine-homocysteine methyltransferase form an abortive ternary complex. Allen et al. (35) showed that methionine production could be inhibited 50% by the addition of 10 µM dimethylglycine in their assays of human betaine-homocysteine methyltransferase activity. These kinetic properties, i.e., a substrate conferring a very low Kcat and whose product is a potent inhibitor, explain why high levels of betaine and dimethylglycine are found in the urine and plasma of hyperhomocyst(e)inemics treated with betaine and why elevated levels of plasma homocysteine persist.

Thetins may be a more effective plasma homocysteine-lowering agents than betaine because they are more specific substrates for betaine-homocysteine methyltransferase and produce products with lower affinities for the enzyme (Example I). Hence, thetins may produce a greater flux through the betaine-homocysteine methyltransferase reaction in vivo resulting in greater reductions in plasma homocysteine than those obtained with betaine.

EXAMPLE 3

Use of Dimethylacetothetin and dimethylpropiothetin in vivo

Dimethylacetothetin and dimethylpropriothetin, like betaine, can replace the dietary requirement for choline in growing rats whose diets lack methionine but contain homocystine (41, 49, 50). Furthermore, thetin consumption was not reported to have any toxic effects. In one study thetins were fed at 0.5–0.93% (w/w) of the diet for 3 to 4 weeks. Food intake and growth were not different among experimental groups consuming either thetin, choline, or betaine as methyl donors. Furthermore, there were no indications of kidney hemorrhage or fatty liver in animals fed any of the methyl donors, including thetins, compared to control animals whose diets lacked any methyl donor. Kidney hemorrhage and fatty liver are classical signs of choline deficiency in rats. In summary, thetins can replace dietary choline or betaine in rodents.

There is considerable data showing that the first step in the metabolism of dimethylacetothetin and dimethylpropiothetin is through the betaine-homocysteine methyltransferase reaction. Subsequent metabolism of the demethylated product of the dimethylpropiothetin-dependent reaction, 3-methylthiopropionate, is through the transamination pathway of methionine catabolism, where it enters below the rate-limiting step. The metabolic fate of demethylated product of the dimethylacetothetin-dependent reaction, methylthioacetate, is not completely understood. When rats were given 60 mg of dimethylacetothetin by either diet or subcutaneous injection, 60% of the sulfur from this compound was found as sulfate in the urine when measured after 24 hours (51). Therefore, thetins can be completely oxidized in mammals.

Methionine is the most toxic of all amino acids required for protein synthesis and its toxicity has been well documented. Very high levels of dietary 3-methylthiopropionate, an intermedate in methionine and dimethylpropiothetin catabolism, produces toxic symptoms identical to those produced by excess methionine consumption. The level of 3-methylthiopropionate that could be produced from the catabolism of dimethylpropiothetin, at levels referred to herein, are well below any level that would be toxic (52).

EXAMPLE 4

Thetins for the treatment of hyperhomocyst(e)inemia

Thetins may be more effective at reducing plasma homocysteine for the treatment of hyperhomocyst(e)inemia than betaine because they are more specific substrates for betaine-homocysteine methyltransferase, their products are weaker inhibitors of betaine-homocysteine methyltransferase than dimethylglycine (see Example I), and they are non-toxic to mammals at levels that would be predicted to be efficacious (see Example II).

It is an object of the present invention to demonstrate the efficacy of dietary thetins as plasma homocysteine-lowering agents using two different rodent models for hyperhomocyst(e)inemia. The folate-depleted rat develops intermediate hyperhomocyst(e)inemia, and cystathionine-β-synthase deficient transgenic mice (homozygous mutant) which develop severe hyperhomocyst(e)inemia. Normal levels of plasma homocysteine in rodents are similar to those of humans. These studies demonstrate the efficacy of thetins relative to betaine.

EXAMPLE 5

Dimethylpropiothetin is found in nature and has osmolyte functions

Thetins are not entirely foreign to nature. Dimethylpropriothetin has been isolated from red algae (53), two family of angiosperms (Gramineae and Compositae; 54), two species of fish (cod and mackerel; 55 and 56), and shellfish (57). Thus, dimethylpropiothetin is already present in the human diet. How much of this compound is consumed by humans in not known and is likely to vary significantly due to cultural variations in diet. Dimethylacetothetin and dimethylpropiothetin were chemically synthesized prior to the discovery of dimethylpropiothetin in nature.

Betaine and dimethylpropiothetin share another related function in living cells. In animal cells, betaine accumulates to very high levels when exposed to environments of high osmolality. Betaine and other compounds that accumulate in such conditions are called osmolytes. These osmolytes allow cells to retain water in environments were the extracellular concentrations of solutes are high. In animals, osmolytes accumulate in the renal medulla. Other compounds that have osmolyte functions in the renal medulla are sorbitol, inositol, and taurine. In some higher plants and marine species dimethylpropiothetin functions as an osmolyte.

Bacteria also accumulate osmolytes when grown in hyperosmotic media. For example, *Escherichia coli* can convert choline to betaine, or accumulate betaine from the environment directly, when grown in environments of high osmolality. It has also been shown that dimethylacetothetin is equally effective as betaine as an osmolyte in *Escherichia coli*.

Betaine has been given to fowl as a means to control diarrhea and wet litter and presumably functions in this capacity as a compatible osmolyte. Dimethylacetothetin and dimethylpropiothetin would function in a similar manner.

EXAMPLE 6

Use of thetins to lower plasma homocysteine or increase methionine synthesis in various clinical situations There are other conditions where thetins may be of clinical value, either because of a need to decrease plasma homocysteine, or increase methionine production. Such conditions include but are not limited to, alcoholism and liver cirrhosis, end-stage renal disease, thyroid disease, antifolate treatment, schizophrenia, and the prevention of neural tube defects.

EXAMPLE 7

Thetins as animal feed additives

Dimethylacetothetin and dimethylpropriothetin, like betaine, have been shown to replace the dietary requirement for choline (or betaine) in growing rats whose diets lack methionine but contain homocystine (41, 49, 50). Therefore, thetins can reduce or eliminate the addition of choline and betaine added to animal feeds while maintaining a similar level of animal performance. These compounds can be made by very simple chemical methods and therefore may improve the cost effectiveness of animal production.

Methionine is an essential amino acid that is limiting in most practical animal feeds to support optimal animal performance. Hence, methionine is routinely added to animal feeds. Nutrition studies have shown that even when sulfur amino acid intake is optimal, only about 70% of the methionine absorbed through the intestine is retained by the animal. This indicates that about 30% of absorbed methionine is either converted to cysteine or completely oxidized. Thetins may be able to reduce the level of methionine that is supplemented to protein-containing animal feeds due to enhanced remethylation of homocysteine to form methionine by the betaine-homocysteine methyltransferase catalyzed reaction. Increasing the efficiency of homocysteine methylation to form methionine would decrease the irreversible oxidation of homocysteine and therefore have a methionine-sparing effect. This would be predicted to increase growth rates and other measures of animal performance while reducing the need for costly methionine supplementation of these feeds.

As a final note, dietary sulfate has been shown to decrease cystine requirements in chickens. Dietary thetins are oxidized to sulfate, and so would be predicted to be cystine-sparing. Practical diets for agriculturally important animals, however, generally contain plethoric levels of sulfate such that thetins would not be predicted to be cystine-sparing in these diets.

It is an object of the present invention to demonstrate the efficacy of dietary thetins as feed additives having methionine-, choline- and betaine-sparing effects when added to practical poultry and swine feeds.

In summary, the present invention defines the role of thetins as specific substrates for betaine-homocysteine methyltransferase that can enhance the conversion of homocysteine to methionine, and as a result, be an effective plasma homocysteine-lowering treatment for animals in need of such treatment. The invention further defines the role of thetins as methionine-, choline-, and betaine-sparing compounds that can be added to animal feeds to reduce the costly addition of these nutrients to feeds while maintaining optimal animal performance.

The following references were cited herein:

1. Koop, C. E., Coronary Heart Disease. In: Surgeon General's Report on Nutrition and Health. PHS Publication number 017-001-00465-1, (1988).
2. American Heart Association, 1992 Heart and Stroke Facts. Dallas, Tex: AHA, (1991).
3. Kang et al., *Annu. Rev. Nutr.* 12: 270, (1992).
4. Ueland et al., Plasma homocysteine and cardiovascular disease. In: Francis RB, ed. Atherosclerotic cardiovascular disease, hemostasis and endothelial function. N.Y.: Marcel Dekker, Inc., 183–236, (1992).
5. Motulsky, A. G., *Am. J. Hum. Genet.* 58:17, (1996).
6. Malinow, MR., *Clin Chem.* 40:173, (1994).
7. Nygard et al., *J. Amer. Med. Assoc.* 274:1526, (1996).
8. National Research Council, Nutrient requirements of poultry, 9th rev. ed. Nat. Acad. Sci., Washington, D.C., (1994).
9. National Research Council, Nutrient requirements of laboratory animals, 4th rev. ed. Nat. Acad. Sci., Washington, D.C., (1995).
10. National Research Council, Nutrient requirements of swine, 9th rev. ed. Nat. Acad. Sci., Washington, D.C., (1994).
11. Mitchell et al., *J. Nutr.* 108:67, (1978).
12. Steele et al., *J. Biol. Chem.* 253:7844, (1978).
13. Mudd et al., *Metabolism* 24:721, (1975).
14. Finkelstein et al., *J. Biol. Chem.* 261:1582, (1986).
15. Finkelstein et al., *J. Biol. Chem.* 259:9508, (1984).
16. Finkelstein et al., *Biochem. Biophys Res. Comm.* 66:81, (1975).
17. Jencks et al., *J. Biol. Chem.* 262:2485, (1987).
18. Yamamoto et al., *J. Nutr. Sci. Vit.* 41:197, (1995).
19. Harper et a., *Amer. J. Physiol.* 184:457, (1956).
20. Finkelstein et al., *Arch. Biochem. Biophys.* 146:84, (1971).
21. Wileken et al., *New Eng. J. Med.* 309:448, (1983).
22. Gahl et al., *J. Inher. Metab. Dis.* 11:291, (1988).
23. Wendel et al., *Eur. J. Pediatr.* 142:147, (1984).
24. Holme et al., *Arch. Dis. Child.* 64:1061, (1989).
25. Maw GA., *Biochem J.* 72:602, (1960).
26. Ericson LE., *Acta Chemica Scand.* 14:2101, (1960).
27. McKeever et al., *Clinical Science* 81:551, (1991).
28. Fromm et al., *Arch. Biochem. Biophys.* 81:363, (1959).
29. Lee et al., *Arch. Biochem. Biophys.* 292:77, (1992).
30. Durell et al., *Biochim. et Biophys. Acta* 26:270, (1957).
31. Sciba et al., *J. Biol. Chem.* 257:14944, (1982).
32. Ericson LE., *Acta Chem. Scand.* 14:2113, (1960).
33. Finkelstein et al., *Biochem. Biophys. Res. Comm.* 108:344, (1982).
34. Finkelstein et al., *J. Nutr.* 113:519, (1983).
35. Allen et al., *Metabolism* 42:1448, (1993).
36. Ericson LE., *Acta Chem. Scand.* 14:2127–2134, (1960).
37. Awad et al., *J. Biol. Chem.* 258:12790, 1983.
38. Finkelstein et al.,*Arch. Biochem. Biophys.* 153:320–324, (1972).
39. Speed et al., *J. Chromatog.* 35:497, (1968).

40. Nelson et al., *J. Chromatog.* 324:203, (1985).
41. Ferber et al., *J. Biol. Chem.* 185:53, (1950).
42. Ip C, et al., *Carcinogenesis* 13:1167, (1992).
43. Finkelstein et al., *J. Biol. Chem.* 242:873, (1967).
44. Hanes C. S., *Biochem. J.* 26:1406, (1932).
45. Garrow TA, et al., *FASEB J.* 9:748, (1995).
46. Fromm HJ., *Mol. Biol. Biochem. Biophys.* 22:83, (1975).
47. Wileken et al., *New Engl. J. Med.* 309:448, (1983).
48. Laryea et al., *Clin. Chim. Acta* 230:169, (1994).
49. Du Vigneaud et al., *J. Biol. Chem.* 131:57, (1939).
50. Maw et al., *J. Biol. Chem.* 176:1037, (1948).
51. Maw GA., *Biochem. J.* 55:42, (1953).
52. Benevenga et al., *Ann. Rev. Nutr.* 4:157, (1984).
53. Patti et al., *J. Nat. Prod.* 56:432, (1993).
54. Rhodes et al., *Ann. Rev. Plant Physiol. Plant Mol. Biol.* 44:357, (1993).
55. Ackman et al., *J. Fish. Res. Bd. Canada* 24:457, (1967).
56. Ackman et al., *J. Fish. Res. Bd. Canada* 29:1085, (1972).
57. Iida et al., *Nippon Suisan Gakkaishi* 52:557, (1986).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of decreasing homocysteine levels in an animal in need of such treatment, comprising the step of administering to said animal a pharmacologically effective dose of a thetin.

2. The method of claim 1, wherein said animal is a human.

3. The method of claim 1, wherein said animal has hyperhomocysteinemia.

4. The method of claim 1, wherein thetin is selected from the group consisting of dimethylacetothetin and dimethylpropriothetin.

5. The method of claim 1, wherein thetin is administered in a dose of from about 1 mg/kg to about 50 mg/kg.

6. A method of treating hyperhomocysteinemia in an animal in need of such treatment, comprising the step of administering to said animal a pharmacologically effective dose of a thetin.

7. The method of claim 6, wherein said animal is a human.

8. The method of claim 6, wherein thetin is selected from the group consisting of dimethylacetothetin and dimethylpropriothetin.

9. The method of claim 6, wherein thetin administered in a dose of from about 1 mg/kg to about 50 mg/kg.

10. An nutritional supplement consisting essentially of a thetin selected from the group consisting of dimethylacetothetin and dimethylpropriothetin and at least one vitamin.

* * * * *